(12) United States Patent
Cebadera Miranda et al.

(10) Patent No.: US 11,827,391 B2
(45) Date of Patent: Nov. 28, 2023

(54) PROCESS AND EQUIPMENT ASSEMBLY FOR ASEPTIC GRAVIMETRIC FILLING OF SOLIDS INTO A CONTAINER

(71) Applicant: LABORATORIOS FARMACÉUTICOS ROVI, S.A., Madrid (ES)

(72) Inventors: Elena Cebadera Miranda, Madrid (ES); Ibon Gutierro Aduriz, Madrid (ES); Maria Garcia Amo, Madrid (ES)

(73) Assignee: LABORATORIOS FARMACÉUTICOS ROVI, S.A., Madrid (ES)

( * ) Notice: Subject to any disclaimer, the term of this patent is extended or adjusted under 35 U.S.C. 154(b) by 905 days.

(21) Appl. No.: 16/585,248

(22) Filed: Sep. 27, 2019

(65) Prior Publication Data
US 2020/0024013 A1    Jan. 23, 2020

Related U.S. Application Data

(63) Continuation-in-part of application No. PCT/EP2018/056968, filed on Mar. 20, 2018.

(30) Foreign Application Priority Data

Mar. 31, 2017    (ES) ............................... ES201730587

(51) Int. Cl.
*B65B 1/32*    (2006.01)
*A61J 3/07*    (2006.01)
(Continued)

(52) U.S. Cl.
CPC .................. *B65B 1/32* (2013.01); *A61J 3/07* (2013.01); *A61K 31/4196* (2013.01);
(Continued)

(58) Field of Classification Search
CPC .... B65B 1/32; B65B 1/06; B65B 3/28; G01G 15/00
See application file for complete search history.

(56) References Cited

U.S. PATENT DOCUMENTS 3,605,826 A * 9/1971 Carter ................... B65B 31/025
141/93
4,640,322 A   2/1987 Ballester
(Continued)

FOREIGN PATENT DOCUMENTS

| EP | 0408822 A2 | 1/1991 |
| EP | 2138447 B1 | 2/2014 |

(Continued)

*Primary Examiner* — Timothy P. Kelly
(74) *Attorney, Agent, or Firm* — INNOVAR, L.L.C.; Rick Matos

(57) ABSTRACT

A system for and method of gravimetric filling of a solid product in sterile conditions in a pharmaceutical container of small dimensions including syringes, vials, capsules, ampoules, single-dose devices, inhalers, bottles, carpules, well(s) of blister pack(s), sachets or bags with solid substances selected from the group formed by powder, lyophilizate, granules, pellets, nanoparticles or microparticles. More particularly, it relates to a process for the gravimetric filling of pharmaceutical containers with one or more sterile solid pharmaceutical substances or sterile excipients dosed and prepared in an aseptic environment.

11 Claims, 4 Drawing Sheets

(51) Int. Cl.
*A61K 31/4196* (2006.01)
*A61K 31/519* (2006.01)
*B65B 1/04* (2006.01)
*G01G 15/00* (2006.01)
*B65B 1/06* (2006.01)
*A61J 1/00* (2023.01)

(52) U.S. Cl.
CPC .............. *A61K 31/519* (2013.01); *B65B 1/04* (2013.01); *B65B 1/06* (2013.01); *G01G 15/00* (2013.01); *A61J 1/00* (2013.01)

(56) References Cited

U.S. PATENT DOCUMENTS

| | | | | |
|---|---|---|---|---|
| 5,322,095 | A * | 6/1994 | Bolz | ........................ B65B 39/08 |
| | | | | 141/93 |
| 5,544,684 | A * | 8/1996 | Robinette, III | ........ G01G 17/06 |
| | | | | 177/25.14 |
| 6,987,228 | B1 | 1/2006 | MacMichael | |
| 8,108,068 | B1 | 1/2012 | Boucher | |
| 2016/0200461 | A1 | 7/2016 | Broadbent | |
| 2018/0155068 | A1* | 6/2018 | Bailey | ........................ B65B 1/32 |

FOREIGN PATENT DOCUMENTS

| | | | |
|---|---|---|---|
| EP | 2832648 | A1 | 4/2015 |
| EP | 2902327 | B1 | 1/2016 |
| WO | 02092430 | A2 | 11/2002 |
| WO | 2006074904 | A2 | 7/2006 |
| WO | 2006075227 | A2 | 7/2006 |
| WO | 2010128455 | A1 | 11/2010 |
| WO | 2012004606 | A2 | 1/2012 |
| WO | 2012023118 | A1 | 2/2012 |
| WO | 2016170474 | A1 | 10/2016 |
| WO | 2016185230 | A2 | 11/2016 |

* cited by examiner

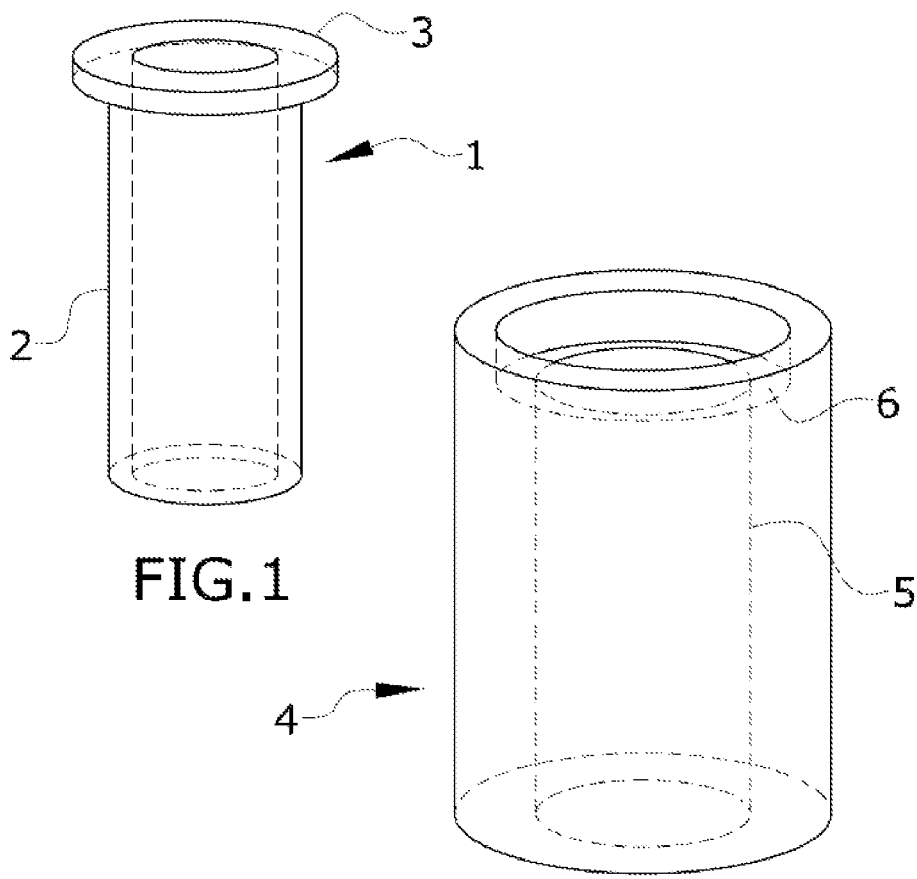
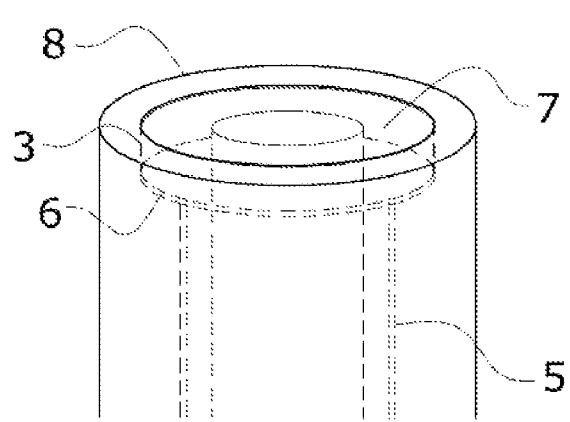
FIG.1
FIG.2
FIG.3

PROCESS AND EQUIPMENT ASSEMBLY FOR ASEPTIC GRAVIMETRIC FILLING OF SOLIDS INTO A CONTAINER

CROSS-REFERENCE TO EARLIER FILED APPLICATIONS

The present application claims the benefit of and is a continuation-in-part of international application PCT/EP2018/056968 filed Mar. 20, 2018, which claims the benefit of Spanish application No. 201730587 filed Mar. 31, 2017, the entire disclosures of which are hereby incorporated by reference.

FIELD OF THE INVENTION

The present invention relates to a process and equipment assembly for sterile (aseptic) gravimetric filling of solid into a container. In some embodiments, sterile solids are charged into one or more pharmaceutical containers of small dimensions including syringes, vials, capsules, ampoules, single-dose devices, inhalers, bottles, carpules, blister packs, sachets, or bags. Exemplary solid substances include particulate solids such as powder, lyophilizate, granules, pellets, particles, beads, nanoparticles or microparticles. More particularly, it relates to a process for the aseptic gravimetric filling of pharmaceutical containers with one or more sterile solid pharmaceutical substances and/or sterile excipients dosed and prepared in an aseptic environment.

BACKGROUND OF THE INVENTION

The legislation for the pharmaceutical industry imposes strict safety conditions on the filling of pharmaceutical containers with pharmaceutical substances. Currently, the filling of pharmaceutical containers of small dimensions such as syringes, vials or carpules among others, with pharmaceutical substances must comply with Good Manufacturing Practices (GMPs). To do this, a controlled airflow is generally used to work in sterile environments.

The movement of a fluid or gas when it is organized, stratified and gentle is called controlled airflow. In a laminar flow, the fluid moves in parallel laminas without mixing together and each fluid particle follows a trajectory called streamline. The controlled airflow may be considered as laminar or turbulent. Reynolds predicted the type of flow we have through an a dimensional parameter called Reynolds number, which represents the ratio between the viscosity and inertia in the movement of a fluid, as is represented by the following equation:

$$Re = Vs \times D/Vc$$

where:
Vc=Kinematic viscosity;
Vs=Characteristic velocity of the fluid; and
D=Diameter of the section wherethrough the fluid circulates.

When Re<2000, the flow is referred to as "Laminar flow", i.e. wherein the viscous forces are proportionally stronger than the forces of inertia and, therefore, the particles tend to move in streamlines. When Re>4000, the flow is referred to as "Turbulent flow", i.e. wherein the viscous forces are weak compared with the forces of inertia and, therefore, the particles move in irregular routes. When 2000<Re<4000, the flow is referred to as "Transitional flow", i.e. it cannot be modelled per se.

The above-mentioned legislation defines controlled airflow as that wherein the streamlines go in one direction, are approximately parallel and have a uniform velocity through the complete cross section of the clean zone. Thus, GMPs indicate velocities between 0.36 m/s and 0.54 m/s (i.e. 0.45 m/s±20%), and they define it as "Unidirectional flow", according to Annex 1 relating to the manufacturing of sterile drugs of Good manufacturing practices for medicinal products for human and veterinary use published by the European Medicines Agency (EMA). According to this guide, the laminar flow systems must provide a homogeneous velocity in the aforementioned range at the working point in an open environment, i.e. where the dosing is performed.

The main function of a unidirectional/laminar flow is to provide a working area free from particles and contamination where it guarantees the protection of critical processes, ensuring total protection of the products during their handling process and an isolation of the surrounding environment.

The protection is produced in the "process core", i.e. in the location where the process and the interaction of the environment with the process occur. This is achieved thanks to the absence of particles by means of a type of filtration called HEPA. HEPA is the acronym of High Efficiency Particle Arresting. It is a high capacity filter which may trap a high quantity of microparticles, such as pollen, dust mites or tobacco smoke. After being filtered through a HEPA filter, the discharged air must have a uniform velocity controlled according to the legislation to be fulfilled (according to the GMPs: 0.36-0.54 m/s). Three factors intervene in this uniformity: the air diffusion screen used, the regulation of the fan velocity and the air channeling and return.

In accordance with the use and design of the laminar flow, it is possible to guarantee the protection of the product, the protection of the operator or the protection of both. In any case, the controlled airflow allows control of the process in a sterile environment, meaning it can do so without additional processes such as terminal sterilization.

When the products that the containers are filled with are liquids, their filling is simpler than for solid products both if performed using a volumetric or gravimetric method. In any case, in the volumetric methods, wherein what is determined is the volume of product to be filled in the container instead of its weight, the product dosing is much simpler as it does not require the presence of a weighing cell which conditions the filling or dosing accuracy, and which may also be altered by the impact of airflow.

Regarding the filling of solid substances such as microparticles, nanoparticles, granules, pellets, powder, etc., in pharmaceutical containers of small dimensions, the problem of gravimetric filling is much greater, because it is essential that the powder flows consistently and predictably, without any type of block or turbulence, thus guaranteeing that the volume or the weight of the solid pharmaceutical substance in the pharmaceutical container is appropriate. And if the filling is also performed under laminar airflow, the problem is even greater, as the laminar flow may influence both the precision of the measurement by the balance, and the flow of solid particles as they are deposited in the container and, therefore, it may alter the result observed in the balance and, in consequence, the quantity of product filled in the container.

In this regard, it is necessary to consider that for the pharmaceutical industry, an error in the filling of the active substance may cause patients to receive an inadequate dose of the product, which may have very harmful or even lethal effects in extreme cases. For this reason, in the processes described in the state of the art it is necessary to regularly check, by means of various previously qualified processes, the effective filling quantity of all the pharmaceutical containers and discard those wherein the quantity of pharmaceutical substance, whether drugs, active substances or excipients, are outside the range.

These tests may be destructive or non-destructive. When they are non-destructive, a control is performed on 100% of the containers filled by gravimetric weighing methods, only discarding those units which are outside the pre-set specification. However, when the tests are destructive, as generally occurs in volumetric filling processes, these controls are performed by means of statistical weighing every short time with the aim of controlling the dosing during the process, which greatly effects the yield of the filling process since all control units are discarded despite the fact that they conform because of the destructive method.

As a consequence, due to the high cost and value of the pharmaceutical substances handled and the fact that they are produced in large batches, it involves a very high financial cost for the pharmaceutical companies to be able to control the accuracy of product dosing, preferably using non-destructive control methods. However, contrary to this precept, the documents of the state of the art that allude to the filling process in small containers, allude to volumetric filling processes that generally perform destructive control processes, which lead to a loss of productivity, or which require multiple weighing controls in a multiplicity of stations or stages, which makes the process excessively expensive. Furthermore, the documents of the state of the art allude to dosing forms in devices or containers with dimensions greater than those used in the present invention.

Publication No. US 2016/0200461 A1 to by VANRX Pharmasystems Inc. discloses a method for the volumetric filling and aseptic sealing of containers such as vials, bottles, syringes and ampoules with a liquid or lyophilized solid pharmaceutical product (which implies that the filling process is performed in liquid phase) in a controlled environment enclosure. A high number of containers are filled at the same time, all of them located in the sealed enclosure. This sealed enclosure where the containers are found is introduced in a seal box, and at least the sealed enclosure or seal box must be decontaminated. The containers are sealed under vacuum or inert atmosphere conditions.

International publication No. WO 2006/074904 to IMA LIFE S.R.L. discloses the packaging of injectable liquid products in containers such as vials, syringes or more preferably bottles, in a sterile environment by means of sterilization and depyrogenating. More specifically, it relates to a complete and compact system for sterile packaging comprising a station for washing the containers intended for cleaning and decontamination of said containers, a sterilizing station to sterilize the containers that exit the washing station, this sterilizing station has two sterilizing modules, each module has in its upper part suitable conduits and separating baffles so that it achieves an airflow that impacts the bottles, said flow flows above the conveyor into a bell, under which are provided filtering means defined by a HEPA filer, both sterilization methods may work as cold or hot sterilizers and, finally, a filling and sealing station for filling said containers with said liquids which are later sealed.

European publication No. EP 2832648 A1 to Grifols Worldwide Operations Ltd. discloses a machine and a method for filling pharmaceutical containers with liquid pharmaceutical compounds which make it possible to eliminate the problem of having to reject pharmaceutical containers, preferably vials, the quantity of pharmaceutical substance of which is outside the range specified in the legislation of the pharmaceutical industry, avoiding for said industry a significant additional cost in terms of investment in the machine proposed by said patent and increasing product productivity. The method comprises the steps of weighing the empty container, filling the container with the pharmaceutical substance and later weighing of the full container in a full-container weighing station to confirm the quantity of pharmaceutical substance.

International publication No. WO 2012/023118 A1 to IMA Industria Macchine Automatiche S.P.A. discloses a filling machine comprising a total weight checking system and a method for individually weighing units. More specifically, the publication discloses a filling machine suitable for filling capsules comprising a total weight check system of the capsules filled with a pharmaceutical product, containing a weighing apparatus for weighing all the capsules and transfer means for transferring the capsules from said filling machine to the weighing apparatus. This machine has, in the case of microdose weighing, an additional electronic balance, which has one or more load cells, for weighing the empty capsules, by means of transfer means the capsules are transferred to filling machines and the full capsules are transported to another weighing apparatus comprising electronic balances equipped with one or more load cells capable of measuring the weight of each full capsule. A laminar airflow is not used during the process nor are aseptic filling conditions contemplated.

U.S. Pat. No. 4,640,322 to Cozzoli Machine Co. discloses a machine for filling containers with particulate matter with certain fluidity, such as powder and similar matters. Principally, the machine applies sub-atmospheric pressure through a filter to suction the particulate material and then, after filling the measuring chamber or, sub-atmospheric pressure is applied through a filter to force the particulate matter downwards within the pharmaceutical container. This patent discloses a volumetric filling process which does not consider the specific properties of the product to be filled without mentioning the repercussion of the filling process subjected to laminar flow.

International publication No. WO 02/092430 to IMA Industria Macchine Automatiche SPA discloses an apparatus for the automated filling of bottles with solid substances in powder or granules, and in particular, it discloses a machine for filling bottles with dosed powdered pharmaceutical substances and to the filling propulsion mechanism which forms part of the machine. This process consists of several stages, the first relates to the weighing of the empty bottles in a first station, then, the bottles are filled in a filling station comprising powder dosing disks and a feed device of the pharmaceutical powder, these bottles pass to a second bottle weighing station for weighing the full bottles, and, finally, to a bottle capping station, all of this by means of a volumetric filling system. This system allows for quick and easy access to the dosing disks without having to remove the adjustment mechanisms, ease of maintenance and cleaning of the machine, and being a process to follow that is faster and less laborious. Logically, this process as it is volumetric only works for pharmaceutical powder with homogeneous granulometry and with a constant apparent density, since it does not guarantee in any way a specific particle size in addition to not allowing the filling of different batches of different chemical nature. Furthermore, despite the fact it mentions that it works in sterile conditions, it does not specify the method used to achieve said sterility, which presupposes terminal sterilization methods after the capping.

European publication No. EP 2902327 B1 to Harro Höfliger Verpackungsmaschinen GmbH discloses a dosing device for the volumetric dosing of pharmaceutical powder and the simultaneous filling of containers such as capsules and blisters among others, with the dosed powder. The device comprises a dosing station with a container for storing the powder, a filling station and a mobile measurement element wherein this measurement element is displaced from the dosing station to the filling station and vice-versa. It also has a sealing material which is elastically flexible, hermetic, porous and air-permeable. The measurement element moves from the dosing station to the filling station with a maintained negative pressure difference, where the dosing cavities are superimposed with the pharmaceutical containers. It eliminates the negative pressure difference and the powder passes from the dosing cavities to the pharmaceutical containers. The measurement element moves gain to the dosing station. In this case, the filling is volumetric so that the dosing is much simpler for those components that do not have specific granulometry to control.

International publication No. WO 2010/128455 A1 to IMA Industria Macchine Automatiche S.P.A. discloses a dosing apparatus and dosing unit associable with an automatic filling machine to dispense pre-set and precise quantities of product in pharmaceutical containers, said machine having means for dosing both liquid and solid substances, which for this purpose, said dosing means comprises: a volumetric piston pump, a peristaltic pump, a diaphragm or membrane pump, a time-pressure dosing system, a flow-control dosing system, a flowrate meter dosing system, a volumetric dosing system for powders or granules. The filling is volumetric so that the dosing is much simpler for those components that do not have specific granulometry to control.

International publication No. WO 2012/004606 A2 to 3P Innovation Ltd discloses a powder doser for pharmaceutical substances comprising a dispensing system including a stirrer formed by flexible material and a hopper wherefrom the powder may flow. This hopper is divided in two parts, a first part formed by a flexible material and a second formed by a rigid material, a piezo-electric vibration device to make the hopper vibrate, and a device for weighing the pharmaceutical containers whilst they are being filled with the powder. Publication No. WO 2016/185230 A2 also to 3P Innovation discloses an apparatus and method for filling pharmaceutical containers such as syringes, vials, capsules, carpules and blisters with pharmaceutical matter in powder by means of vibration. This apparatus has a support for the pharmaceutical container, a reservoir to contain powdered pharmaceutical substances, which is in contact with a filling needle responsible for filling the pharmaceutical container with the powdered pharmaceutical substance, and a piezoelectric vibration device. None of these publications by 3P Innovation Ltd mentions the physicochemical and rheological properties of the formulation components, and they are always centered on a vibration filling system, so that the solution proposed for the technical problem is exclusively limited to vibration filling machines and eliminating the impact of the harmful effects of said vibration in the drug dose. In no case do they suggest any other filling type that is not vibratory, since they disclose as essential element a vibration buffer part to be able to control the powder filling process. Furthermore, said publications do not include examples of embodiments that enable validating the suitability of the claimed filling system. Moreover, the degree of vibration to which the system is subjected together with the velocity and force of the airflow the filling process is subjected to make the precise powder filling process in the container absolutely unfeasible in addition to its weighing, since they have no elements that prevent the loss of verticality of the container so that it remains suitable so that the nozzle between the container facilitating the dosing or that the container remains vertically suspended (without touching the walls of the vibration buffer part) so that the weighing device can guarantee the pre-set dose.

European publication No. EP 2138447 A1 to I.M.A Industria Macchine Automatiche S.P.A. discloses a machine for the production of vials and bottles, particularly, for the filling of vials and bottles with doses of pharmaceutical product in liquid or powder form. This machine comprises a station for feeding the open vials or bottles in an upper end or mouth, a filling station of the vials or bottles with predetermined product dose, a station for feeding a succession of seals for sealing the mouth of the vial or the bottle, a station for applying the seals to the vials or bottles and feeding them in a collection area and, optionally, there may be an additional weighing station of the vials or bottles. All the components are disposed within a sterile environment, whereby sealing units are used to create a sterile environment in the machine for the production of the vials or bottles. There machine concerns a system for filling powder into containers, generally bottles and vials, by means of a vibration filling process which does not consider the necessary granulometry of the formulation components.

U.S. Pat. No. 6,987,228 B1 issued Jan. 17, 2006 to MacMichael discloses an apparatus and method for dispensing small quantities of particles. U.S. Pat. No. 8,108,068 B1 issued Jan. 31, 2012 to Boucher discloses a prescription medication control system and method. EP 0408822 A2 published Jan. 23, 1991 to Takeda Chemical Industries LTD discloses a filling apparatus for automatically filing very small amounts of drugs. WO 2016170474 A1 published Oct. 27, 2016 to IMA SPA discloses an apparatus and method for filling containers with pharmaceutical ingredients.

International publication No. WO 2006/075227 A2 to IMA Industria Macchine Automatiche SPA discloses a unit for sterilizing and depyrogenating empty containers, mainly bottles. Said sterilization and depyrogenating is carried out by selecting as desired from the four possible combined sterilization modes: hot-cold, hot-hot, cold-hot and cold-cold. The process is performed with the empty bottles, which after said process will be transported to a filling phase with the material in liquid or powder, which is not mentioned in said document. Their system only employs a sterilization and depyrogenating station for empty container suitable to be filled in a later process, which is not mentioned.

In general terms, the above publications disclose the filling of pharmaceutical containers but without considering the physicochemical or rheological properties of the products (so that they consider neither the filling of various products of different nature in the same dosing process or apparatus), nor the necessary and normalized process conditions for the aseptic filling of pharmaceutical products, particularly without considering those cases where the environment wherein the process is performed is an aseptic environment, with a gravimetric filling subjected to laminar flow. In the case of the above publications which largely use volumetric filling, this process has a series of drawbacks that are intensified when the dosed product is a solid, such as process inaccuracy, unreliability of substance dosing where there are substances of different granulometry or nature, the need to constantly calibrate the doser depending on the material before each use and the incapacity of automatically compensating for the changes in the properties of the material, preventing filling several different products in the same apparatus or process, such as oscillations in the apparent density of the packaged products. Therefore, volumetric methods are unsuitable when there are variations in the apparent density inter batch, or when in a single product there is heterogeneity in granulometry, as it cannot guarantee that the content throughout the batch is homogeneous. Furthermore, volumetric methods may alter the integrity of the substance dosed depending on the nature of the product, so it may form agglomerations, and more so if we consider that these processes are highly dependent on the filling temperature and viscosity of the product, generating insurmountable fluctuations in the dose accuracy.

However, weighing and dosing control is vital for certain drugs, since they require a gravimetric filling process in the containers that respects the nature of the solid, in addition to the distribution of the particle size of the active agents and/or the solid excipients that form part of the formulation.

These aspects require that for some types of drugs, such as sustained release drugs or inhalers, volumetric methods are not suitable, and they require gravimetric filling processes, with the aim that once the suitable quantity of each one of the components is dosed, there is a dispensing of the active substance in the composition in addition to an active diffusion phenomenon of the agent within the release system originating a controlled-release phenomenon of the active substance in the formulation. If, furthermore, we consider the sustained-release systems and inhalers—which need to guarantee the correct release and/or activity of the formulation with the passage of time,—its make it more necessary if possible to control the dosing with the granulometric properties to guarantee the activity of the formulation throughout the prescription time period, so that small dose variations give rise to shorter or longer lasting activities than those prescribed, which obliges said formulations to be rejected from the production chain.

The filling process of a solid pharmaceutical formulation in a pharmaceutical device or pharmaceutical container must overcome several difficulties. In the first place, it is necessary in many cases to dose a very small quantity of product with great accuracy. To this first point, we have to add the need to comply with the legislation indicated in the different international pharmacopoeias for aseptic fillings where the presence is necessary of large airflow streams (unidirectional or turbulent flow), which guarantee the elimination of any particle foreign to the process that may contaminate the end product. These two conditions are essential for achieving the proposed aim (aseptic filling of solid in pharmaceutical devices), but achieving this is unfeasible on many occasions, since the presence of large airstreams harms and alters the precise dosing.

This fact is further complicated if possible when we refer to a gravimetric filling process, wherein the only unit of measurement and dose control is the weight, and the incidence of airstream inside the device, during or after the dosing, may cause the displacement of the solid, impregnating the walls thereof and even escaping to the outside (preventing the accuracy of the dose). This problem is aggravated if the filling is performed by gravimetric control (by weight), since the air will affect the sensor element and also distort the measurement.

This fact is important, since the basic function of industrial filling systems is to dose predetermined quantities of solids in a specific time period and precisely. Therefore, the important thing is not the volume but the mass of the product to dose. In contrast, the result of dosing depends on other variables such as the physicochemical characteristics of the bulk product, the granulometry of the solid, the conditions of the environment and the dosing process in relation to the selected dosing body. With respect to the process, the principle of volumetric dosing should be differentiated from gravimetric dosing.

In volumetric dosing, the expulsion of the material is exclusively produced in accordance with the volume and, with the quantities. In other words, the volume is defined before the powder dosing starts. In this way, as the dosers that work volumetrically do not measure the mass, their dosing bodies will have to be calibrated depending on the material before each use: it is necessary to determine what quantity of must be dosed by the body in a defined time period. The same is also applied when the material and the batch are changed. Furthermore, volumetric dosing systems cannot automatically compensate for the changes in material properties, such as oscillations in apparent density, viscosity, distribution of particle size, and even the nature of the different solid products. Thus, with the aim of compensating for the possible oscillations in the pouring weight, volumetric systems often operate with overdosing since its operation depends on the volume so that the doser body is always uniformly filled. It is for this reason that a weighing of the volumetric dosing system is more compatible with the laminar flow system, it becomes totally unfeasible in the case of sophisticated drugs that have determined granulometric and physicochemical properties.

Hence, volumetric filling has a series of drawbacks that are intensified when the dosed product is a solid, such as the inaccuracy of the process, the unreliability of the substance dosing when there are substances of different granulometry or nature, the need to constantly calibrate the dose depending on the material before each use and the inability to automatically compensate for the changes in the material's properties, preventing filling several different products in the same apparatus or process, such as variations in the apparent density of the packaged products. Therefore, volumetric methods are unsuitable when there are inter batch variations in the apparent density in a single product, or when in a single product there is heterogeneity in the granulometry as it may not guarantee that the content in all the production batch is homogeneous. Furthermore, the volumetric methods, may alter the integrity of the dosed substance depending on the product nature as agglomerations may form and more so if we take into consideration that these processes are highly dependent on the filling temperature and product viscosity, generating insurmountable fluctuations in the dose accuracy.

However, in the principle of gravimetric dosing or in accordance with the weight, one or several weighing cells integrated in the process measure (weigh) the material that one wants to dose. Therefore, the only unit of measurement is the weight. So that the actual weight regulates the dosing, meaning that gravimetric systems can automatically compensate for the possible deviations in apparent density, in addition to other characteristics intrinsic to the product such as the distribution of particle size of the solid. Logically, the gravimetric dosing system is practically incompatible with the laminar flow system, since the incidence of an airstream inside the device, and in particular in, on or in the surrounding area of the weighing cell during or after dosing, may cause several drawbacks in the process: the displacement of the solid impregnating the walls thereof and even escaping to the outside (preventing accuracy of the dose), the impact of the airstream in the sensor element or weighing cell, distorting the measurement, affecting the cleaning of the inside of the device, alteration of the integrity of the dose filled and consequent contamination, alteration of the distribution of particle size since the flow disperses the particles of smaller size varying the homogeneity of batches, etc.

Therefore, one of the challenges to overcome when performing an aseptic filling is the protection of the filling process from the incidence of airstreams that the aseptic conditions require in the case of drugs, preferably, parenteral drugs. Hence, it is necessary to create an area of exclusion where the dosing process is protected from said streams. Thus, both the sterility of the process and the accurate dosing by weight are preserved, since on the one hand it isolates the weighing cell (allowing the correct gravimetric dosing) and on the other hand, around this small area of exclusion (limited environment around the pharmaceutical device during the filling) the effect of the airstream continues to prevail (of turbulent or unidirectional flow) avoiding the access of any viable particle (with capacity to generate microbiological colonies or not) or infeasible (any impurity or particle foreign to the product product) to the interior of the device or container.

This area of air exclusion around the filling process must only exist during said filling process, so that the incidence of the streams on all the system surfaces is possible the rest of the time. Thus, it preserves the aseptic character provided that this is possible, minimizing the risk of contamination and eliminating microbial contamination from the pharmaceutical formulation.

At present, to achieve the sterility of pharmaceutical products, pharmaceutical containers are generally subjected to a terminal sterilization process generally carried out with humid heat in an autoclave, by means of which the pharmaceutical containers are steam sterilized. However, this process is unsuitable for sterilizing solid pharmaceutical products since, as water vapour is produced in this type of sterilization, it damages the integrity of the solid product that absorbs humidity. Furthermore, this type of sterilization does not manage to penetrate in the powder, so that it would not give rise to the sterilization of the pharmaceutical product that there is within the pharmaceutical container. This sterilization process also has several drawbacks such as deterioration of the material used in the process, the difficult control monitoring during the process, in addition to the long period of time used in the sterilization that may alter the physicochemical properties of the product.

SUMMARY OF THE INVENTION

The present invention seeks to provide a process and equipment assembly (apparatus) for overcoming one or more disadvantages of the prior art systems. The present invention concerns processes and equipment for gravimetric filling of solids into containers. The present invention more particularly concerns filling of pharmaceutical containers with solid pharmaceutical substances by means of a gravimetric filling process with, or without, laminar flow in an aseptic environment. The invention can be adapted for the gravimetric filling of nanogram-scale, microgram-scale, milligram-scale, gram-scale, or kilogram-scale amounts of material(s) into respective container(s). In preferred embodiments, the invention is adapted for the gravimetric filling of nanogram-scale, microgram-scale, milligram-scale, and/or gram-scale amounts of material(s) into respective container(s).

An object of the present invention is to provide a process for the gravimetric filling or dosing of solid substances into containers, e.g. pharmaceutical containers, pharmaceutical dosage form containers.

An object of the invention is to provide a process for the gravimetric filling or dosing of solid substances into small containers, in particular for the gravimetric filling or dosing of pharmaceutical substances into pharmaceutical containers. In some embodiments, the process is an aseptic gravimetric filling process for charging precise dose(s) of one or more pharmaceutical ingredient(s) into one or more pharmaceutical containers.

An aspect of the invention provides a gravimetric filling system in a laminar airflow operational space comprising one or more receivers adapted to provide respective one or more contained (enclosed) non-laminar flow spaces within which respective one or more containers (to be charged with material and to be weighed) can be placed, whereby when said gravimetric filling system is exposed to laminar air (gas) flow, said laminar air (gas) flow does not enter said one or more contained spaces during charging and weighing of said one or more containers.

An aspect of the invention provides a method for gravimetric filling of one or more containers, said method comprising the following steps: a) providing one or more receivers adapted to provide respective one or more contained (enclosed) non-laminar airflow spaces within which respective one or more containers (to be charged (or filled or dosed) with material and to be weighed) are disposed; b) charging one or more materials into said one or more containers; and c) weighing said one or more containers with said one or more materials; wherein the exterior of said one or more receivers is exposed to laminar air (gas) flow during said charging and/or weighing step(s), whereby said laminar airflow does not enter said one or more contained non-laminar airflow spaces nor said one or more containers during said charging and/or weighing step(s).

An aspect of the invention provides a method for gravimetric filling of a container, said method comprising:
providing a gravimetric filling apparatus comprising at least one lid (comprising at least one charging port), at least one receiver (for receiving container(s)), and at least one gravimetric system (comprising at least one weighing element and at least one non-weighing surface);
placing at least one container in said receiver and assembling said at least one lid, said at least one receiver, and said at least one gravimetric system, thereby defining a contained (confined) space within which said at least one container is disposed, whereby said at least one container rests on said at least one weighing element (disposed within said contained space) but does not rest on a horizontal surface of said at least one receiver;
charging an amount of at least one material through said at least one charging port and into said at least one container; and
determining the combined weight of said at least one material and a respective container.

In some embodiments, said at least one container comprises at least one flange and a respective receiver comprises at least one receptacle for said flange, wherein the diameter and height of said receptacle is larger than the respective diameter and height of said flange.

In some embodiments, the process further comprises at least one of or one or more of the following steps: a) neutralizing the electrostatic charge of at least one of the container, receiver, lid, gravimetric system, and material; b) purging the contained space with gas or air prior to or after charging of material; c) placing under vacuum the contained space prior to, during, or after charging of material; d) taring the container resting upon the weighing element prior to charging material into the container; e) sterilizing the container and material in the container; f) charging (dosing) a predetermined amount of material into the container; g) providing at least one sleeve (spacer) between the container and a respective receiver; h) transferring the receiver to the weighing surface (system, element); i) charging a predetermined amount of material into each of plural containers; j) charging more than one material into a container; k) charging a mixture of two or more materials into a container; l) placing a plunger within the container after charging material into the container; m) vibrating the container; n) exposing the exterior of said at least one lid and said at least one receiver to laminar airflow before, during, and/or after said charging step, whereby said laminar airflow does not enter said contained space; o) purging the contained space with gas or air prior to or after weighing of said container(s); p) conducting said process as an aseptic gravimetric filling process; q) transferring said container(s) having said material(s) to a sealing operations area; r) transferring said receiver(s) with respective ones of said container(s) having said material(s) to a sealing operations area (sealing station(s)); and/or s) sealing said container(s) containing said material(s).

More particularly, the invention relates to a process for the gravimetric filling in pharmaceutical containers of one or more sterile solid pharmaceutical substances dosed and prepared in an aseptic environment with controlled airstream (airflow, gas flow) so that the measurement of the weight is precise and is not influenced by the presence or absence said airstream. In some embodiments, laminar air (gas) flow is not required or does not occur within the contained space during the charging and weighing step(s). In some embodiments, laminar airflow occurs at the exterior but not at the interior of said receiver or container during gravimetric filling (charging and weighing).

In some specific embodiments, the solid substance is a particulate solid selected from the group consisting of powder, lyophilizates granules, beads, pellets, nanoparticles, microparticles, nanospheres, and microspheres. In some specific embodiments, the pharmaceutical container is a small container. In some embodiments, the container is selected from the group consisting of syringe, vial, capsule, ampoule, single-dose device, inhaler, bottle, carpule, well(s) of blister pack, sachet and bag.

In some embodiments, the invention more particularly relates to a process for the gravimetric filling of pharmaceutical containers with one or more sterile solid pharmaceutical substances dosed and prepared in an aseptic environment with controlled airstream so that the measurement of the weight is precise and is not influenced by the presence or absence of laminar flow.

An advantage of the present invention is that it does not require weighing the pharmaceutical container both before and after filling with the solid pharmaceutical substance in plural stations, meaning in other than the dosing station, since the present invention defines a gravimetric filling process wherein the weighing cell (weighing element, load cell) is located in the container filling station, which means it can be confirmed that, after taring the container, the quantity of solid pharmaceutical substance it is filled with is precise. In some embodiments, the empty container(s) is(are) weighed at the same operational station which serves as both a weighing station and a filling station.

The process of the present invention is capable of being used in an aseptic environment in all its stages, filling the containers by a gravimetric process subjected to controlled laminar or turbulent flow, meaning that the type of airflow used does not alter the product weighing, thus avoiding the drawbacks produced by said flow such as the disturbance or prevention of the precise solid filing in the pharmaceutical containers.

An aspect of the invention provides an operational station in an equipment assembly, said operational station comprising a gravimetric filling system under laminar airflow, said gravimetric filling system comprising one or more receivers adapted to provide respective one or more contained (enclosed) non-laminar airflow spaces within which respective one or more containers (to be charged with material and to be weighed) can be placed, whereby said laminar airflow does not enter said one or more contained non-laminar airflow spaces nor said one or more containers during charging (filling) and weighing of said one or more containers.

The present invention has the additional advantage of achieving precision-filling of several substances of different nature into a single container from at least one filling station, in this way managing to fill more than two solid compounds of a different nature without interaction between them, since they are in solid form, and the degree of humidity of the end product is less than 10%. This advantage is very important, since the humidity may alter the weighing and cause the formation of agglomerations in the products, something which would alter the dose weighed in the container and which would alter the rheology of the compounds dispensed in the containers.

Advantageously, throughout the process of the present invention, it is possible to maintain an aseptic environment that guarantees the sterility of the finished pharmaceutical product without requiring a terminal sterilization step, in particular without requiring terminal sterilization in an autoclave or in pressurized humid heat. The disadvantages of terminal sterilization are overcome with the present invention, since an aseptic environment is maintained whilst the pharmaceutical containers are filled with sterile solid pharmaceutical substances, which guarantees sterility of the end pharmaceutical product during the process and at the end thereof. The invention thus also provides a process for aseptic gravimetric filling of solid into one or more containers, said process excluding a heat-based, steam-based, or gas-based terminal sterilization step conducted after filling of said one or more containers. In some embodiments, the process further comprises the step of sterilizing the charged material by irradiation (gamma or beta radiation).

In some embodiments, the container-to-container variability of material charged into the containers exhibits a standard deviation of ±30% or less, ±20% or less, ±10% or less, ±5% or less, ±2.5% or less, or ±1% or less.

The invention is suitable for use with pulverulent solid compounds of possessing substantially any particle size distribution. In some embodiments, the solid exhibits a particle size distribution defined as follows: no more than 10% of the total volume of particles is less than 20 microns, no more than 10% of the total volume of particles is greater than 230 nor less than 140, and a value d0.5 in the range of 60-160 microns, wherein d0.5 indicates the mean value of the particle size that divides the population exactly in two equal halves, with 50% of the distribution above this value, and 50% below. In general, throughout this specification, a value called "d0.X" represents the fraction in mass of the drug with particle sizes below the specified value, having a range from 0.0 to 1.0. According to this definition, a value of d0.1 of 10 microns means that 10% of the total particle mass of the drug has a particle size less than or equal to 10 microns.

An aspect of the invention provides a gravimetric filling apparatus for use in gravimetric filling of one or more containers, said apparatus comprising the following:
  a) at least one receiver for said one or more containers, said receiver(s) comprising a respective receptacle adjoining a respective chamber (for receiving said one or more containers), a first end, and a second end;
  b) at least one lid for respective one(s) of said one or more receiver(s), said lid(s) comprising at least one charging port and said lid(s) being disposed at said first end; and
  c) at least one gravimetric system comprising a non-weighing surface and at least one abutment (mount, projection, cup, stand, platform) directed into said respective chamber(s) and adapted to raise said one or more containers when said container(s) is/are disposed within said chamber(s), and disposed at said second end,
  thereby forming contained space(s) defined by said at least one receiver, said at least one lid, and said non-weighing surface, said contained space(s) adapted for receiving said one or more containers, and said contained space(s) being accessible through said charging port(s) for charging material therethrough into said one or more containers.

During operation of said gravimetric filling system (apparatus, equipment assembly), it is optionally exposed to laminar airflow to assist in maintaining an aseptic (cleanroom) environment; however, during the operational steps of charging material(s) into the container(s) and weighing the container(s) having said material(s), the laminar airflow does not enter the contained space(s) defined by the receiver(s) even when the remaining part(s) of the gravimetric filling system are being exposed to the laminar airflow.

In some embodiments, the gravimetric filling apparatus is further defined by at least one of or one or more of the following: a) said receptacle has a larger diameter than said chamber; b) the length of said container combined with the height of said abutment is less than the length of said contained space; c) the apparatus is adapted for gravimetric filling of containers comprising one or more flanges (ridges), wherein the spatial volume of said receptacle is greater than the spatial volume of said flange; d) the spatial volume defined by the outer surfaces of said container is less than the spatial volume defined by the inner surfaces of said contained space; e) the apparatus is adapted for gravimetric filling of containers comprising one or more flanges (ridges), wherein the height and outer diameter of said flange is less than the height and inner diameter of said receptacle; f) exposing the exterior but not the interior, of said at least one receiver to laminar airflow during the gravimetric filling (charging and weighing of material); and/or g) exposing said gravimetric filling apparatus, but not the interior of said at least one receiver, to laminar airflow before, during and/or after said gravimetric filling (charging and weighing of material). In some embodiments, the at least one abutment comprises one or more weighing elements.

Another aspect of the invention provides an apparatus (equipment assembly) adapted for use in (optionally aseptic) gravimetric filling of containers. In some embodiments, the invention provides an apparatus (15) comprising:
  a hollow receiver (4) having a height (4H) and comprising: a) an inner cavity (4A) having a first length (4L) and a first inner diameter (4ID), said receiver having a first outer diameter (4OD); and b) a receptacle (6) disposed at an upper end of said inner cavity, said receptacle having a first height (6H) and a second inner diameter (6ID), and said receptacle being defined by a lower surface (6A) and a circumferential surface (6B), wherein 4OD>6ID>4ID;
  a container (16) comprising: a) a body having a length (16H) and an outer diameter (16OD) and an inner cavity; and b) a flange (3) disposed adjacent to or at an upper end of said body, said flange (or ring or ridge) having a second height (3H) and a second outer diameter (3OD), and said flange being defined by a lower surface (3A) and a circumferential surface (3B), wherein 3OD>16OD and 16H>3H; and
  a lid (12) having a charging port therethrough, said lid having an outer diameter (12OD), whereby the smallest outer diameter of said lid is sufficiently large such that the lid covers at least the entire opening of the receptacle;
  wherein: 6ID>3OD>4ID; and 4H>16H and 6H>3H.

In some embodiments, the apparatus further comprises a gravimetric weighing system (9) comprising a non-weighing surface (10) and a mount (11, projection, abutment, cup, stand, platform) associated with said non-weighing surface (10). The mount has a height (11H) and an outer diameter (11OD), wherein: a) 4H>(16H+11H); and b) 4ID>11OD.

In some embodiments, said mount comprises at least one weighing element (load cell) that weighs the container and material charged into the container.

The hollow receiver can have two open ends prior to being placed on the non-weighing surface and prior to be covered by the lid. In some embodiments, when said hollow receiver, said container, said lid, and said gravimetric weighing system are assembled, the lower surface of said flange (3) is spaced away from said lower surface (6A), the upper surface of said flange is spaced away from the lower surface of said lid, and said circumferential surface (3B) is spaced away from said circumferential surface (6B).

When said hollow receiver, said container, said lid, and said gravimetric weighing system are assembled, they define a contained spaced within which laminar airflow does not enter during the charging and weighing steps. The upper end of the receiver is covered by (or is in close proximity to) the lid and the lower end of the receiver contacts (or is in close proximity to) the non-weighing surface.

In some embodiments, when said hollow receiver, said container, said lid, and said gravimetric weighing system are assembled, the lower surface of said flange (3) is spaced away from said lower surface (6A) by the distance (S1), the upper surface of said flange is space away from the lower surface of said lid by the distance (S2), and said circumferential surface (3B) is spaced away from said circumferential surface (6B) by the distance (S3).

In some embodiments, the apparatus of the invention further comprises one or more sleeves (spacers) disposed between the outer surface of the container (1, 16) and the inner surface of the cavity of the receiver (4).

In some embodiments, 12OD>6ID. In some embodiments, 12OD>4OD>6ID.

In some embodiments, the hollow receiver (4) contacts (or engages) said non-weighing surface (10) and the lower surface of said lid (12) thereby forming a contained space within the receiver, said contained space having the container therein.

In some embodiments, the apparatus (equipment assembly) further comprises at least one of or one or more of the following: a) at least one control system (B1, B2 of FIG. 5. That controls the amount of material charged into said one or more containers; b) at least one material charging system (B3, B5) for charging material into said one or more containers; c) at least one laminar airflow system (B8A, B8B); d) at least one deionizer (A1-A7); e) at least one transfer system (B9A, B9B) for transferring the material-containing container, with or without its respective receiver, to another operational area; or f) a combination of any two or more thereof.

In some embodiments, the gravimetric filling process is conducted in a sterile environment in a closed or open space. Preferably, the equipment assembly, as either individual components or as a whole, are under aseptic conditions, such as by being placed in one or more isolators or being placed in sterile operating area(s), e.g. a cleanroom. The atmospheric pressure of the space surrounding the assembly will typically be positive, meaning above ambient pressure. The atmospheric temperature of the space surrounding the assembly will typically be at ambient or less than ambient temperature, e.g. ≤80° F., ≤75° F., ≤70° F., ≤65° F., ≤60° F., or ≤55° F. In some embodiments, the relative humidity of the operating space within which the equipment assembly is placed ranges from about 30% to about 60% or about 10% to about 60%.

Another aspect of the invention provides a method of preparing a pharmaceutical kit comprising at least the following: a) a first container comprising solvent(s); and b) a second container comprising particulate drug(s) and particulate polymeric carrier(s); said method comprising at least the following step(s) in any order: aseptically filling and weighing said particulate drug(s) and said particulate polymeric carrier(s) into a container by employing an aseptic gravimetric filling system (apparatus or equipment assembly) and/or method according to the invention; sealing said container, thereby providing said second container; providing said first container; and packaging said first container and said second container, thereby providing said pharmaceutical kit.

The specification discloses one or more embodiments that incorporate features of this invention. The scope of the present invention is not limited solely to the disclosed embodiments. The invention includes all combinations and sub-combinations of the various aspects and embodiments disclosed herein. These and other aspects of this invention will be apparent upon reference to the following detailed description, examples, claims and attached figures.

BRIEF DESCRIPTION OF THE FIGURES

The accompanying figures, which are incorporated herein and form a part of the specification, illustrate one or more embodiments of the present invention and, together with the description, further serve to explain the principles of the present invention and to enable a person skill in the pertinent art to make and use the invention. The following drawings are given by way of illustration only, and thus are not intended to limit the complete scope of the present invention.

FIG. 1 depicts a front perspective view of the container (1) used in the present invention. The container comprises a hollow body (2) (e.g. cylinder or tube) and a ridge (3, flange) disposed adjacent to or at one end of said hollow body.

FIG. 2 depicts a front perspective view of the hollow receiving-cylinder (4, receiver) used also in the present invention, showing its inner cavity (5) and the recess (6, receptacle) disposed adjacent to or at the upper end of said inner cavity (5).

FIG. 3 depicts a partial front perspective of the container (1) inserted in the receiving-cylinder (4), so that the flange (3) of the container (1) rests on/in the lower surface defining the receptacle (6) of the cylinder (4), so that the only area of contact between container (1) and cylinder (4) is a lower surface of the flange and the lower surface defining the receptacle.

FIG. 4 also depicts the lid (12) adapted to cover the unit (adapted to seal the open end of the cylinder (4)) so that it is hermetically isolated from the outside.

DETAILED DESCRIPTION OF THE INVENTION

Figure 4:
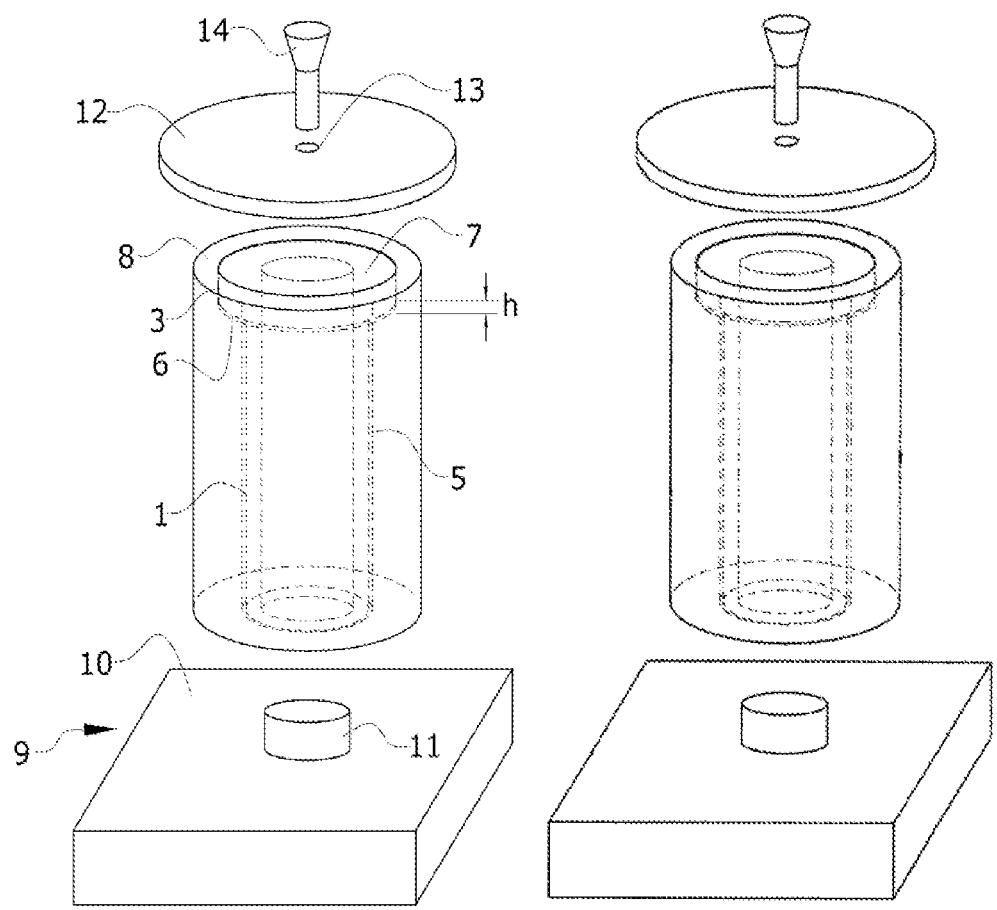
FIG. 4 depicts a front perspective view of the cylinder (4) and container (1) unit inserted therein, when both parts are about to be located above the gravimetric weighing system (9) which is equipped, on its non-weighing surface (10), with a mount (11). When the cylinder (4, receiver) and container (1) unit are lowered, the projection contacts the container (1) thereby slightly raising it from its resting-position in the recess (6) of the cylinder (4) so that it is totally in suspension above the mount (11), resting all its weight on the projection, whereby the gravimetric weighing system (9) can accurately measure the weight of the container (1).

The invention provides a method of gravimetric filling of a solid product in a container, the method comprising the following steps, which are illustrated in attached FIGS. 1 to 4:
  a) providing a container (1) comprising a generally cylindrical body (2) and which is equipped in its upper part with a ridge (3, flange) of diameter slightly greater than the diameter of the body (2) of the container (1);
  b) inserting the container (1) in a hollow cylinder (4), the inner cavity (5) of which has a diameter slightly greater than the diameter of the body (2) of the container (1), and which is equipped with a recess (6, receptable) in the upper area of the inner cavity (5), so that the ridge (3) of the container (1) rests in the recess (6) of the upper area of the inner cavity (5) of the cylinder, and with the contact area between the ridge (3) of the container (1) and the recess (6) of the upper area of the inner cavity (5) of the cylinder being the only area of contact between container (1) and cylinder (4), so that the container (1) is in suspension within the inner cavity (5) of the cylinder (4) and with its upper surface (7) located slightly underneath the upper surface (8) of the cylinder;
  c) placing the cylinder (4) and container (1) unit above a gravimetric weighing system (9) which is provided on its non-weighing surface (10) with a mount (11, weighing element) which has a diameter less than the diameter of the inner cavity (5) of the cylinder (4) and a suitable height to raise the container (1) by the sufficient height (h) so that the ridge (3) of the container is no longer in contact with the recess (6) of the upper area of the inner cavity (5) of the cylinder (4) but without the upper surface (7) of the container (1) exceeding the height of the upper surface (8) of the cylinder (4), so that the container (1) is disposed above and rests upon the mount (11) provided on the non-weighing surface (10) of the gravimetric weighing system (9) and therefore resting all its weight thereon;

d) covering the upper surface (8) of the cylinder (4) hermetically by means of a lid (12) equipped with an orifice (13) wherethrough it is possible to add the solid product by means of a dosing element (14) or nozzle;

e) weighing with the desired precision the container (1) while it is disposed above and rest its weight upon the mount (11), and f) filling the container (1) with the solid product through the orifice (13) of the lid (12), gravimetrically controlling the quantity of product added thereto by means of the gravimetric weighing system (9).

The lid of step d) must be understood in general terms as any element which may hermetically cover the cylinder (4), so that, for example, said lid may be implemented in the practice in the form of the lower walls or of a flexible hopper which incorporates a dosing element or nozzle, provided that this hopper is adapted to the cylinder so that it does not allow the access of airflow therein but still allows charging of material into the container.

Steps e) and f) are preferably performed in the same dosing station with the object that the precision of the weighing is optimum, although nothing would prevent it from being performed in different dosing stations.

Through the steps of the method described, the vertically elevated position of the container (1) is achieved so that the container (1) does not touch the inner walls of the cylinder (4), so that the weighing device may precisely guarantee the pre-set weight of added solid product. Furthermore, said vertically elevated position renders is possible for the dosing element (14, solids charging device) or nozzle to enter the container (1) and facilitate the dosing (charging). All of this may occur even in the presence of vibration provided by an external vibrating element, which in embodiments of the invention may help correctly dose the product in the container (1).

The invention also provides an apparatus (equipment assembly) adapted for use in aseptic gravimetric filling of containers. In some embodiments, the invention provides an apparatus (15) comprising:

a hollow receiver (4) having a height (4H) and comprising: a) an inner cavity (4A) having a first length (4L) and a first inner diameter (4ID), said receiver having a first outer diameter (4OD); and b) a receptacle (6) disposed at an upper end of said inner cavity, said receptacle having a first height (6H) and a second inner diameter (6ID), and said receptacle being defined by a lower surface (6A) and a circumferential surface (6B), wherein 4OD>6ID>4ID;

a container (16) comprising: a) a body having a length (16H) and an outer diameter (16OD) and an inner cavity; and b) a flange (3) disposed adjacent to or at an upper end of said body, said flange (or ring or ridge) having a second height (3H) and a second outer diameter (3OD), and said flange being defined by a lower surface (3A) and a circumferential surface (3B), wherein 3OD>16OD and 16H>3H; and a lid (12) having a charging port therethrough, said lid having an outer diameter (12OD), whereby the smallest outer diameter of said lid is sufficient large so that lids covers the receptacle entirely;

wherein: 6ID>3OD>4ID; and 4H>16H and 6H>3H.

Figure 6:
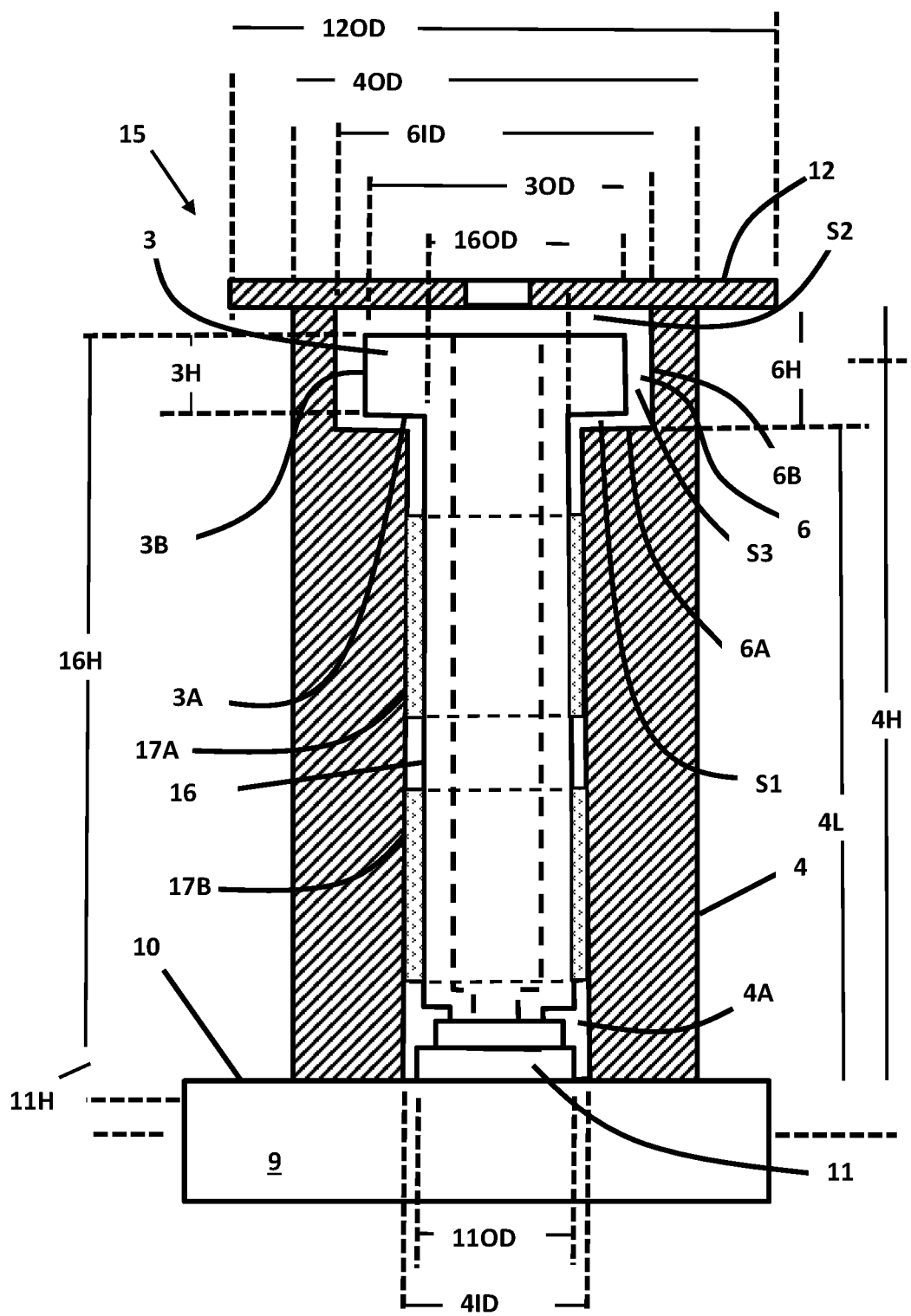
FIG. 6 depicts a partial sectional front elevation view of an equipment assembly (15) of the invention.

In the exemplary embodiment of FIG. 6, the container can be a carpule, ampoule, bottle, vial, syringe or other such container having a flange or ring. In this exemplary embodiment, the apparatus further comprises a gravimetric weighing system (9) comprising an upper surface (10) and a mount (11, projection, weighing element, load cell). The mount has a height (11H) and an outer diameter (11OD), wherein: a) 4H>(16H+11H); and b) 4ID>11OD. When said hollow receiver, said container, said lid, and said gravimetric weighing system are assembled, the lower surface of said flange (3) is spaced away from said lower surface (6A), the upper surface of said flange is spaced away from the lower surface of said lid, and said circumferential surface (3B) is spaced away from said circumferential surface (6B). In particular embodiments, when said hollow receiver, said container, said lid, and said gravimetric weighing system are assembled, the lower surface of said flange (3) is spaced away from said lower surface (6A) by the distance (S1), the upper surface of said flange is space away from the lower surface of said lid by the distance (S2), and said circumferential surface (3B) is spaced away from said circumferential surface (6B) by the distance (S3). The inner dimensions and shape of the inner cavity (4A) of the hollow receiver (4) and the outer dimensions and shape of the outer surface of the container (16) are adapted to ensure the container remains vertical and spaced away from the hollow receiver yet enclosed within the inner cavity (4A) during the weighing operation.

In some embodiments, the apparatus of the invention further comprises one or more sleeves (spacers (17A, 17B), as described further herein) disposed between the outer surface of the container (1, 16) and the inner surface of the cavity of the receiver (4).

In some embodiments, the apparatus further comprises a vibrating element or system, external to the receiver.

In some embodiments, 12OD>6ID. In some embodiments, 12OD>4OD>6ID. The hollow receiver (4) contacts (or engages) said upper surface (10) and the lower surface of said lid (12). The purpose of the lid is to temporarily seal (except for the existence of the materials charging port in the lid) the receptacle and cavity of the receiver after the container has been placed within the receiver, whereby laminar airflow cannot enter the contained spaced during the charging and weighing steps.

In a preferred embodiment, the process is carried out in an isolator, meaning the equipment assembly or apparatus is placed in an isolator. In another preferred embodiment, the process is carried out in a sterile open room (meaning the equipment assembly or apparatus is placed in said room), e.g. a cleanroom or restricted area barrier system (RABS), complying with in both cases Grade A according to the classification of clean air rooms and devices commonly accepted by standard EN ISO 14644-1.

In the case of isolators, and according to a preferred embodiment, before the dosing operation stated in the present invention, it requires a sterilization with nebulized or vaporized hydrogen peroxide or a mixture of hydrogen peroxide with peracetic acid. In some embodiments, the process of the invention further comprises sterilizing at least one of said isolator, said container, and said receiver prior to charging of material into said container. Said sterilizing can be carried as described herein or using a method accepted for use in the pharmaceutical industry.

In some embodiments, the pharmaceutical substance is a particulate solid, which can be selected from the group consisting of powder(s), lyophilizate(s), granule(s), bead(s), particle(s), pellet(s), nanoparticle(s), nanosphere(s), microsphere(s), and microparticle(s). In some embodiments, the container is selected from the group consisting of one or more syringe(s), one or more vial(s), one or more capsule(s), one or more ampoule(s), one or more single-dose device(s), one or more inhaler(s), one or more bottle(s), one or more carpule(s), one or more well(s) of blister pack(s), one or more sachet(s), and one or more bag(s).

The method (aseptic gravimetric filling and weighing process) and apparatus (equipment assembly) of the invention provide numerous advantages over other methods for filling containers, esp. small pharmaceutical containers, with sterile solid(s).

- The cylinder (receiver), possessing the herein described characteristics, and retaining the container and which is temporarily hermetically closed before the weighing, achieves hermetic isolation of the container from the laminar airflow in the measurement cabin and, therefore weighing, of both the full and empty container, is no longer be affected by the existence of laminar flow.
- Likewise, the product to be filled in the container, in addition to its access channel (the charging port in the lid) thereto, is also isolated from the outside hermetically, so that the laminar flow in the measurement cabin cannot affect the falling of the solid product in the container either.
- The empty container is weighed under essentially the same conditions and normally only with seconds of difference before it starts being filled with the solid product, thereby avoiding or minimizing potential errors that might occur when the weighing is performed at different moments and/or circumstances of the process.
- With the container and receiver designed as described herein, it is possible to very precisely dose solids that have certain characteristics such as apparent density, intrinsic viscosity, specific distribution of particle size of the solid, etc. aseptically under laminar flow conditions.

For the person skilled in the art, it will be clear that the process indicated may be implemented in different embodiments of the invention, all of which are hereby included within the scope of the invention and according to the content of the attached claims. For example, and without limiting character, the present invention includes the particular embodiments, all independent from one another but they may be combined together without limitation.

In some embodiments, one or more "sleeves" is/are disposed between the container and cylinder (receiver) provided said sleeves do not interfere with the process of the invention. The one or more sleeves may provide additional advantages such as a better balance of the container within the cylinder cavity. Illustratively, a "sleeve" of this type between container and cylinder may have a height of between 0.5 mm and 10 mm, and preferably between 0.5 and 5 mm in height. This "sleeve" provides suitable verticality or suspension of the container in the receiver, so that the container remains in a suitable position when the dispenser needle (nozzle, solids dispenser) enters through the lid and the top of the container facilitating the dosing. In addition, the container remains suspended vertically (without touching the walls of the vibration buffer part), so that the weighing device (weighing system/element) can provide an accurate weight of the pre-set (predetermined) dose charged into the container.

In another embodiment, the cylinder (receiver) may be equipped with additional external surface features, such as an outer ridge of a certain thickness, adapted to allow the cylinder to rest without the risk of the cylinder sliding or falling and/or adapted to allow the cylinder, with said ridge, to be transferred from one place to another within the different points of the filling stations, such as by means of a series of elevated rails.

In a further embodiment, the projection (abutment, mount, load cell, weighing cell, cup) provided on the weighing (gravimetric) surface may have a generally cylindrical form but may also adopt any other form such as square, hexagonal or others, when viewed from a top plan view or side elevation view. The projection can be symmetric or asymmetric. Its upper surface may also be flat or may end in other geometric forms, such as conical or truncated cone shaped. All these variations may be possible as long as the projection continues to fulfil its function of raising (elevating) the container, optionally covered by one or more sleeves, sufficiently so that the ridge (flange) of the container is separated from the recess of the upper surface of the cylinder so that all the weight of the container, with or without product, rests on the projection and therefore on the balance (weighing system), thereby essentially guaranteeing correct weighing thereof (before and after charging of solid therein). It is also important that the height of the projection not be too high to ensure that the upper surface of the container (mounted on the projection) does not rise above the upper surface of the cylinder (receiver, receptacle of the receiver), because if the upper surface of the container is above the upper surface of the cylinder, hermetic sealing of the cylinder by means of the indicated lid would be prevented.

Referring to FIG. 6, 4H must be greater than the sum of 11H+16H, and 6H must be greater than 3H. The inner diameter 6ID of the receptacle (6) of the receiver must be greater than the outer diameter 3OD of the flange (3) of the container (carpule, syringe, bottle, vial, etc.) (16) (see FIG. 6). Likewise, the inner diameter 4ID of the cavity in the retainer (4) must be greater than the outer diameter (16OD) of the hollow body of the container (16).

In some embodiments, the invention provides a method and apparatus for aseptic gravimetric filling of at least one container. The invention also provides a method and apparatus for aseptic gravimetric filling of two or more containers, i.e. of plural containers. The filling can be done sequentially, simultaneously or in an overlapping manner.

The product filling stage may be repeated as many times as necessary, for example if more than one different product is filled in the container, the different products can be filled in the container in different filling stages. Alternatively, if there were no reasons to keep the different solid products in different or separate stages, it would also be possible to previously mix the different products and charge the solids mixture into one or more containers in a single filling stage and weighing in a single weight measurement.

In some embodiments, the invention provides an aseptic gravimetric filling method further comprising the step of ionizing and/or neutralizing the electrostatic charge of one or more containers. The apparatus (equipment assembly) of the invention can further comprise one or more ionizers that neutralize (or discharge or dissipate) the electrostatic charge, if present, of one or more containers.

For example, one or more filling steps may be accompanied, previously, subsequently and/or simultaneously, with one or more ionization steps of the container to neutralize its electrostatic charges. Ionization (electrostatic charge neutralization) can be achieved by employing one or more ionizers. Exemplary ionizers can comprise devices selected from the group consisting of bar, needle, curtain, filter, ring, and etc. This ionization step allows the solid product to falls in the form of powder into the container, particularly when the container is made of plastic material, whereby the particles of the solid (e.g. powder) should not adhere to the inner or outer walls of the container and instead fall to the bottom thereof.

In some embodiments, the method of the invention further comprises the step of filling solid into one or more containers under a stream of sterile inert gas (e.g. nitrogen, or air). In some embodiments, the apparatus (equipment assembly) of the invention further comprises a source of sterile inert gas, a source of sterile air, or a combination of the two. In some embodiments, the inert gas is filtered through a high efficiency particulate (HEPA) air filter. In some embodiments, the equipment assembly further comprises a nitrogen generator and/or a source of compressed nitrogen gas.

As used herein, the term "airflow" or "air flow" is considered to encompass "gas flow", e.g. "inert gas flow", whereby laminar airflow is taken to also include laminar gas flow. Accordingly, the term "laminar flow" is taken to include laminar airflow and laminar gas flow.

For example, the filling of the product(s) into one or more containers may be simultaneously accompanied with a gaseous stream, which is preferably sterile $N_2$ gas or sterile compressed air, to facilitate dosing and provide the necessary sterility conditions required by the process. Furthermore, when the airstream is $N_2$ it displaces some, most, or all of the oxygen present inside the container, thereby preventing or minimizing oxidation of the product and its subsequent oxidative degradation. The flowing gas can flow outside the exterior of the receiver but will preferably not flow within the sealed receiver during the charging and weighing operations, thereby essentially maintaining aseptic conditions during such operations without having the laminar airflow interfere with the charging and weighing operations.

In some embodiments, the method of the invention further provides the step of charging solid(s) into the container by way of one or more dosing devices independently selected at each occurrence from the group consisting of a) endless screw, b) a weight loss based gravimetric doser further equipped with a hopper and a high-precision nozzle, c) single-thread doser, d) double-threaded doser, e) vibrating channel based doser, f) vibrating hopper, g) doser with equipped with conveyor belt, h) doser equipped with a solids compacting system, and i) other such solids charging devices.

In some embodiments, the apparatus (equipment assembly) of the invention further provides one or more solids charging devices (dosing devices), for charging solid into the container, independently selected at each occurrence from the group consisting of a) endless screw, b) a weight loss based gravimetric doser further equipped with a hopper and a high-precision nozzle, c) single-thread doser, d) double-threaded doser, e) vibrating channel based doser, f) vibrating hopper, g) doser with equipped with conveyor belt, h) doser equipped with a solids compacting system, and i) other such solids charging devices.

In yet another additional embodiment, the doser (dosing device, solids charging device) may be equipped with a mixer.

In some embodiments, the method of the invention comprises the step of filling plural containers with one or more solid(s). In some embodiments, the apparatus (equipment assembly) of the invention comprises two or more receivers as described herein. In some embodiments, the apparatus (equipment assembly) of the invention comprises a receiver comprising two or more inner cavities and two or more respective receptacles as described herein.

For example, the cylinder (receiver) of the present invention may be equipped with plural inner cavities each of which has a diameter slightly greater than the diameter of the body of the container it is adapted to receive. Each cavity is adjacent a respective receptacle in the upper area so that the respective ridges (flanges) of the containers rest in the respective receptacles, and the contact area between the ridge of each container and of each recess of the upper area of the cavity of the cylinder being the only area of contact between container and cylinder, whereby, prior to weighing, each container is in within each cavity of the cylinder, and the upper surface of each container is vertically disposed slightly below the upper surface of its respective receptacle.

In some embodiments, the weighing system comprises one or more weighing cells (load cells). In some embodiments, the weighing system comprises plural weighing cells, whereby plural containers can be filled and weighed. In another embodiment, the weighing cell is a high-precision cell, preferably impermeable to water, environmental dust, vapors, disinfecting agents, etc.

The pharmaceutical container is preferably charged (filled) while the container is in a vertical position. If a container has a wider end and a narrower end, solids can be charged preferably through the wider end; however, solids can also be charged through the narrower, provided that the inner diameter of the narrower end allows access of the filling needle or nozzle inside the container.

In some embodiments, the equipment assembly further comprises one or more deionizers adapted to eliminate the electrostatic charge of the container and/or receiver so that adherence of powder to the wall of the container and/or receiver during the loading and weighing operations is minimized or eliminated. The use of deionizer(s) minimizes the risk of adherence of powder to the closure surface of the container, such that no powder is on said surface when a cap is placed thereon downstream in the process.

Figure 5:
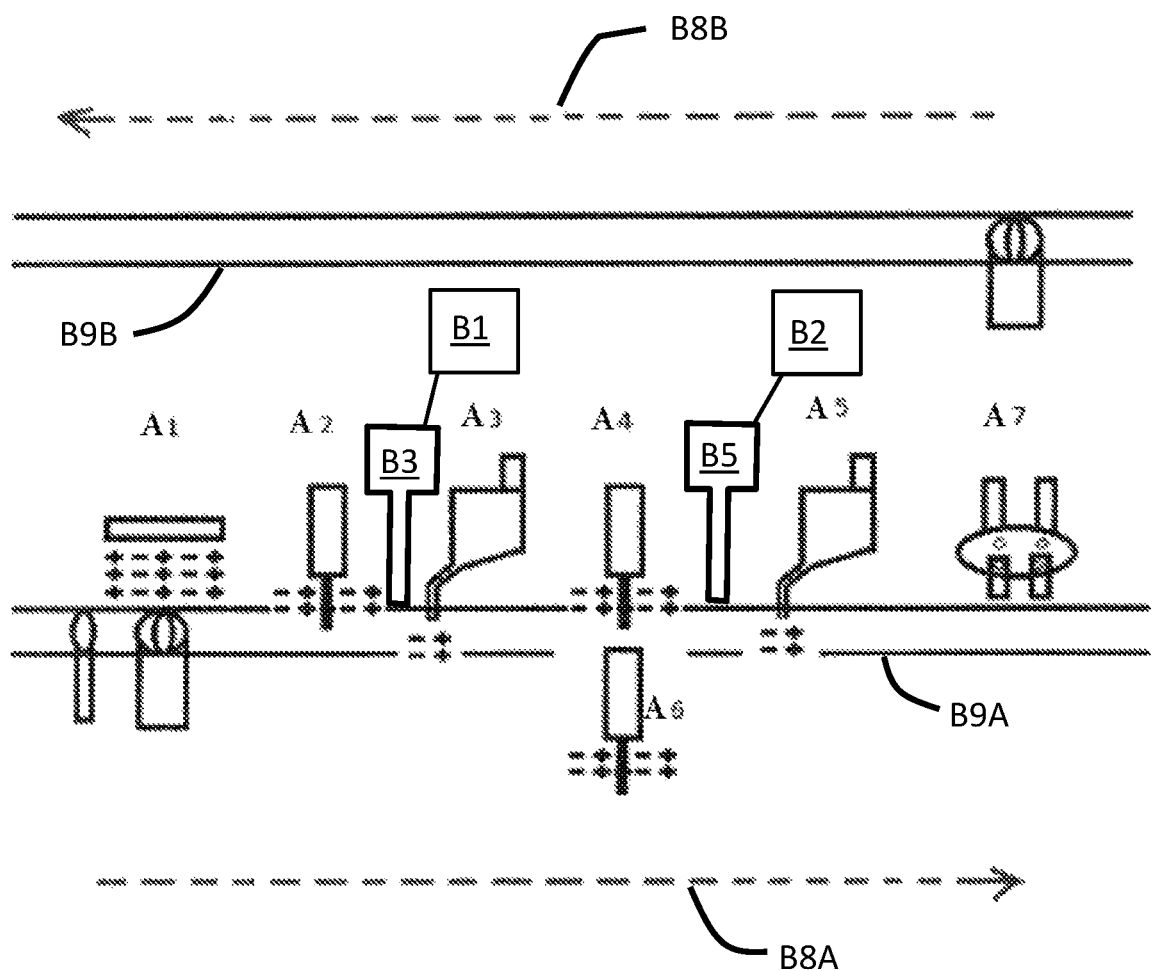
FIG. 5 depicts an illustrative diagram of the different stages which may be present in the filling process according to the invention and which may comprise, according to the illustrative example shown in the figure, the following: (A1): neutralization of electrostatic charges of the container by means of an ionizing bar; (A2): neutralization of electrostatic charges of the container by means of an ionizing needle; (A3) neutralization of electrostatic charges of product A to be dosed, and dosing thereof; (A4): neutralization of electrostatic charges of the container after the dosing of product A; (A5) neutralization of electrostatic charges of product B to be dosed, and dosing thereof; (A6): neutralization of electrostatic charges of the container after the dosing of product B; (A7): capping of the container.

An exemplary overall diagram, included as an illustrative purpose or by way of example, of the part of the process incorporating plural deionizers is depicted in FIG. 5, which depicts a generalized filling-line with various stations (A1-A7). The stations (A1-A7) employs various types of deionizers. The exemplary stations are defined as follows: Station A1—pucks charging station; Station A2—pre-filling station; Station A3—filling station; Stations A4 and A6—prefilling station; Station A5—second filling station; and Station A7—stoppering station.

Station A1 employs a bar deionizer that eliminates the electrostatic charge on the surface of the receiver(s). Stations A2, A4, A6 and A7 employ needle-type (needles) deionizer(s) that eliminates the electrostatic charge on the surface of the container(s). Stations A3 and A5 employ pointing deionizer(s). The transport of ions generated by the electrode of an ionizer, at each of the stations, can be facilitated by use of flowing nitrogen gas or air, either of which can act as a conduit for the ions. The use of such flowing gases is optional.

Each container is independently selected at each occurrence from the group consisting of syringe(s), vial(s), capsule(s), ampoule(s), single-dose device(s), inhaler(s), bottle(s), carpule(s), well(s) of blister pack(s), sachet(s), and bag(s). In some preferred embodiments, the container is a syringe or a carpule. In such cases, the ridge (flange) described above is the ridge that the syringes or the carpules usually have in their upper end, i.e. at the end whereby the plunger or plug of the carpule, respectively, is introduced.

The flange of a container can be permanently or removably attached to the hollow body of the container. The flange can have a height and outer diameter smaller than the height and inner diameter of a respective receptacle in which the container is placed.

The invention also includes embodiments wherein the container (syringe or carpule) is filled by the opposite end, i.e. by the end with the smaller diameter wherethrough the needle would normally be coupled.

A container can be made of any pharmaceutically acceptable material. Exemplary materials include one or more metals, one or more polymers, one or more composites, one or more glasses, crystal, combinations thereof, or any inert (with respect to the solid to be charged into the container) material. Exemplary polymers include polyolefins and cyclic polyolefins, polypropylene, polybutadiene, polyethylene, polystyrene, vinyl polychloride, polyacrylonitrile, polyamides etc., polyesters (containing the ester functional group in its main chain: poly(ethylene terephthalate), polycarbonate), acrylic polymers (poly(methyl methacrylate), polyacrylonitrile), thermoplastic resins (polyacetals and polyhaloethylenes), polyurethanes, formaldehyde resins (phenol resin, urea resin), phenoplasts, aminoplasts, thioplasts, duroplastic resins (unsaturated polyester, polyurethanes), silicones, polyvinylidenes, cellulose derivatives, polycarbonates, and mixtures of two or more thereof, etc. Alternatively, the receptacle may also be metal, e.g. of steel or titanium suitable for the administration of drugs.

The cylinder (receiver) is preferably composed of a metal material such as steel or titanium, although the invention contemplates the possibility that it can be made from various materials, such as different polymer(s), glass, stone, resin, crystal, etc. A preferred material may be a coating that minimizes the formation of electrostatic charge.

Both the materials used for the container and the cylinder materials are preferably gas impermeable, water impermeable, inert, solvent impermeable, and do not absorb and/or adsorb the solid(s) within the container.

Preferably, the container of the present invention is a syringe or carpule. The nozzle (tip, end) thereof preferably comprises a threaded narrow end (male or female) or nonthreaded narrow end (cone, tip). The end can be adapted to engage a needle. In some embodiments, the end is sealed with a rubber (or silicone) stopper (diaphragm, septum) and a cap securing the stopper to the end.

In some embodiments, the invention further comprises the step of placing a plunger within the syringe or carpule after material has been charged. In some embodiments, the container further comprises a plunger disposed within the container containing material.

The invention described herein is useful for aseptic gravimetric filling and weighing of any solid small enough to fit within a respective container, such as within a pharmaceutical container. Exemplary solids include pulverulent solid compounds of any type or composition.

In some embodiments, the solid possesses a particle size distribution defined as follows:

no more than 10% of the total volume of particles is less than 20 microns,
no more than 10% of the total volume of particles is greater than 230 nor less than 140,
a value d0.5 in the range of 60-160 microns,
where d0.5 indicates the mean value of the particle size that divides the population exactly in two equal halves, with 50% of the distribution above this value, and 50% below. In general, throughout the present specification, a value called "d0.X" represents the fraction in mass of the drug with particle sizes below the specified value, having a range of 0.0 to 1.0.

In a first preferred embodiment of the invention, the particle size distribution of the solid is defined as follows:
no more than 10% of the total volume of particles is less than 20 microns,
no more than 10% of the total volume of particles is greater than 230 nor less than 140,
a value d0.5 in the range of 60-130 microns.

In a second preferred embodiment of the invention, the particle size distribution of the solid is defined as follows:
no more than 10% of the total volume of particles is less than 20 microns,
no more than 10% of the total volume of particles is greater than 325 nor less than 245,
a value d0.5 in the range of 100-155 microns.

The method and apparatus (equipment assembly) of the invention need not be limited to pharmaceutical ingredients. In some embodiments, the solid(s) charged into the container is/are a pharmaceutical excipient(s) (or combination thereof), drug (medicament, active agent, pharmaceutically active ingredient, or combination thereof), or a combination thereof.

Suitable drugs include, by way of example and without limitation, risperidone, paliperidone, fentanyl, olanzapine, letrozole, aripiprazole, anastrozole, asenapine, brexpiprazole, cariprazine, clozapine, iloperidone, lurasidone, quetiapine, ziprasidone, etc. A derivative, metabolite or salt of drug can be used. Exemplary drug salt(s) (such as pamoate or palmitate) can be used. Said materials can be used alone or in combination.

The invention described here is applicable to pulverulent solid compounds of any nature.

A particular embodiment of the invention concerns the preparation of containers for use in preparing injectable depot compositions such as those described in U.S. Ser. No. 10/085,936, U.S. Ser. No. 10/182,982, U.S. Ser. No. 10/058,504, U.S. Ser. No. 10/195,138, Pub. US 2015/0147398A1, Pub. US 2015/0150791A1, U.S. Ser. No. 10/285,936B1 and related patents and applications, the entire disclosures of which are hereby incorporated by reference. In said patent documents, the injectable depot composition can be prepared from a kit of two or three different containers. According to one embodiment, a first container comprises organic solvent, a second container comprises drug, and a third container comprises polymeric pharmaceutical excipient. According to another embodiment, a first container comprises organic solvent, and a second container comprises drug and polymeric pharmaceutical excipient.

A particular embodiment of the invention provides a kit comprising a sealed pharmaceutical container comprising drug and polymeric excipient or a kit comprising a sealed container comprising drug and a sealed container comprising polymeric excipient. The sealed container can be independently selected upon each occurrence from a carpule, syringe, vial, bottle, etc. The drug and polymeric excipient can be provided in solid form or liquid form.

According to a particular embodiment, the polymeric excipient is a solid. Any pharmaceutically acceptable polymer can be employed in the invention. Exemplary polymeric excipients include lactic acid homopolymer (PLA), glycolic acid homopolymer (PLG), and poly(lactic acid)-co-poly (glycolic acid) copolymer (PLGA). Preferred exemplary PLGA copolymer include those with a ratio of lactic/glycolic monomer ratio in the range of 40:60 to 70:30, preferably in the range of 45:55 to 75:25.

Other exemplary polymeric excipients include polydioxanone, polytrimethylene-carbonate in the form of copolymers and homopolymers, poly(e-caprolactone) copolymers, polyanhydrides and polyorthoesters, which have been accepted as materials of biomedical use. The polymers may be of synthetic, semi-synthetic and/or natural origin. Combinations thereof are contemplated. They also include cellulose derivatives (for example, cellulose acetate, ethylcellulose, cellulose acetate phthalate, cellulose ethers such as, for example, hydroxypropyl methylcellulose), acrylate derivatives (for example Eudragit, poly(methyl methacrylate), cyanoacrylates) and biocompatible and biodegradable polymers such as polyanhydrides, polyesters, polyorthoesters, polyurethanes, polycarbonates, polyphosphazenes, polyacetals, polyoxyethylene-polyoxypropylenes. Polyesters such as polylactic, polyglycolide, polycaprolactone, polyhydroxybutirate or polyhydroxyvalerate are important. Furthermore, polysaccharides such as sodium alginate, chitosan or chitin or proteins may also be used. Other pharmaceutically acceptable, cosmetically acceptable, or GRAS materials are suitable for use according to the invention.

The preferred polymeric excipients in this invention are selected from copolymers with an intrinsic inherent viscosity preferably in the range of 0.16-0.60 dl/g, and more preferably between 0.25-0.55 dl/g, measured in chloroform at 25° C. and a concentration of 0.1%. The concentration of the polymeric component in the compositions of the invention is preferably included in the range of 25-50%, (expressed as the percentage of polymer weight based on the total polymer solution component) and more preferably between 30-40%.

For the purpose of the present invention, throughout this specification, the term intrinsic or inherent viscosity ($\eta_{inh}$) of the polymer is defined as the ratio of the natural logarithm of relative viscosity, ($\eta_r$), with respect to the polymer mass concentration, c, i.e.: $\eta_{inh} = (\ln \eta_r)/c$ considering that the relative viscosity ($\eta_r$) is the ratio of the viscosity of the solution $\eta$ with respect to the viscosity of the solvent $\eta_s$, i.e.:

$\eta_r = \eta/\eta_s$

Furthermore, it shall be understood that the values of intrinsic viscosity throughout the present specification are measured at 25° C. in a chloroform solution with a concentration of 0.1%. The term of the intrinsic viscosity is commonly considered an indirect indicator of the polymer's molecular weight. In this way, a reduction in the intrinsic viscosity of a polymer, measured at a given concentration in a certain solvent, with the same composition of monomer and terminal groups, is an indicator of the reduction in molecular weight of the polymer (IUPAC. Basic definitions of terms relating to polymers 1974. Pure Appl. Chem. 40, 477-491 (1974).

The following examples illustrate the invention and should not be considered as defining the full scope thereof.

EXAMPLES

Several examples of container filling by means of the process of the present invention are shown below, which must be considered as solely illustrative purposes and not limiting of the scope of the invention. To explain said examples, it should be mentioned that syringes (or carpules) are used as pharmaceutical containers with a female or male connection system indifferently, and PLGA and PLA as polymeric excipients, and Risperidone and Letrozole, respectively, as pharmaceutically active compounds.

Example 1

Sterile Filling of Letrozole into a Syringe

The compound to be charged into the syringe is Letrozole (50 mg dose) to provide a prefilled syringe. The filling process takes place within a TESLTAR AZBIL® rigid-walled aseptic isolator. Before starting with the filling process, all equipment is cleaned and sterilized. Sterilization is performed with nebulized or vaporized hydrogen peroxide or a mixture of hydrogen peroxide with peracetic acid.

Provide sterile syringes and caps (at capping station). Each syringe is placed beneath an ionized nitrogen stream, preferably, although a compressed airstream can be used, to achieve its ionization and elimination of the electrostatic charge. Then, the syringe is moved to the filling station and placed within the cylinder (4). The syringe is placed above the weighing cell, which tares the weight of the empty syringe and records the data in the weight tracker of the control system. After this, the syringe is filled with a quantity of 50 mg±30% of letrozole by means of a nozzle. The syringe is weighed as it is filled during the filling, so that the system can control filling and stop the filling when the desired weight is reached, in this case 50 mg±30% of letrozole.

Subsequently, if a second substance, such as an excipient, is to be charged into the cylinder (4), the syringe filled with letrozole is transported to a second filling station, and the same steps described above are repeated, replacing the letrozole with the excipient.

After filling is complete, the cylinder (4) together with the syringe is passed through an ionization station and then transferred to the capping or sealing station. The sealed syringed is placed on a tray with the other filled and sealed syringes.

This example has been performed for doses of 50, 75, 100, 200, 300, 400 and 500 mg of letrozole, operating suitably and precisely dosing.

Example 2

Sterile Filling of Risperidone into a Syringe

The compound to be charged into the syringe is risperidone (100 mg dose) to provide a prefilled syringe. The filling process takes place within a TESLTAR AZBIL® rigid-walled aseptic isolator. Before starting with the filling process, all equipment is cleaned and sterilized. Sterilization is performed with nebulized or vaporized hydrogen peroxide or a mixture of hydrogen peroxide with peracetic acid.

Provide sterile syringes and caps (at capping station). Each syringe is placed beneath an ionized nitrogen stream, preferably, although a compressed airstream can be used, to achieve its ionization and elimination of the electrostatic charge. Then, the syringe is moved to the filling station and placed within the cylinder (4). The syringe is placed above the weighing cell, which tares the weight of the empty syringe and records the data in the weight tracker of the control system. After this, the syringe is filled with a quantity of 100 mg±30% of risperidone by means of a nozzle. The syringe is weighed as it is filled during the filling, so that the system can control filling and stop the filling when the desired weight is reached, in this case 100 mg±30% of risperidone.

Subsequently, if a second substance, such as an excipient, is to be charged into the cylinder (4), the syringe filled with risperidone is transported to a second filling station, and the same steps described above are repeated, replacing the risperidone with the excipient. See Example 4 for preparation of syringes charged with risperidone and PLGA copolymer.

After filling is complete, the cylinder (4) together with the syringe is passed through an ionization station and then transferred to the capping or sealing station. The sealed syringed is placed on a tray with the other filled and sealed syringes.

This example has been performed for doses of 50, 75, 100, 200, 300, 400 and 500 mg of risperidone, operating suitably and precisely dosing.

Example 3

Sterile Filling of Poly(Lactic Acid) (PLA) into a Syringe

The compound to be charged into the syringe is PLA (90 mg dose) to provide a prefilled syringe. The filling process takes place within a TESLTAR AZBIL® rigid-walled aseptic isolator. Before starting with the filling process, all equipment is cleaned and sterilized. Sterilization is performed with nebulized or vaporized hydrogen peroxide or a mixture of hydrogen peroxide with peracetic acid.

Provide sterile syringes and caps (at capping station). Each syringe is placed beneath an ionized nitrogen stream, preferably, although a compressed airstream can be used, to achieve its ionization and elimination of the electrostatic charge. Then, the syringe is moved to the filling station and placed within the cylinder (4). The syringe is placed above the weighing cell, which tares the weight of the empty syringe and records the data in the weight tracker of the control system. After this, the syringe is filled with a quantity of 90 mg±30% of PLA by means of a nozzle. The syringe is weighed as it is filled during the filling, so that the system can control filling and stop the filling when the desired weight is reached, in this case 90 mg±30% of PLA.

Subsequently, if a second substance, such as an excipient, is to be charged into the cylinder (4), the syringe filled with PLA is transported to a second filling station, and the same steps described above are repeated, replacing the PLA with the excipient.

After filling is complete, the cylinder (4) together with the syringe is passed through an ionization station and then transferred to the capping or sealing station. The sealed syringed is placed on a tray with the other filled and sealed syringes.

This example has been performed for doses between 90 and 1000 mg of PLA, operating suitably and precisely dosing.

Example 4

Sterile Filling of Poly(Lactic Acid)-Co-Poly(Glycolic Acid) Copolymer (PLGA) into a Syringe Containing Risperidone After charging risperidone into syringes according to Example 2 and prior to sealing said syringes, the syringe is passed to a second filling station within the cylinder (4). The syringe is placed above the weighing cell, which tares the weight of the syringe containing risperidone, recording the data in the weight tracker of the control system. After this, the syringe is charged with quantity of 100 mg±30% of PLGA (Resomer 503®) by means of a nozzle. The syringe is weighed as it is filled during the filling, so that the system can be controlled to stop the filling when the desired weight is reached, in this case 100 mg±30% of Resomer 503®.

Subsequently, if a third substance, such as an excipient or another active compound, is to be charged into the cylinder (4), the previously filled syringe is transported to the next filling station, performing the same steps described above as many times as necessary.

After being filled with PLGA, the cylinder (4) together with the syringe is passed through an ionization station and then transferred to the capping or sealing station. Once the syringe is filled and sealed, it is placed on a tray with the other filled and sealed syringes.

This example has been performed for doses of 100 to 500 mg of PLGA, and 50, 75, 100, 200, 300, 400 and 500 mg of risperidone operating suitably and precisely dosing.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

As used herein, the term "about" or "approximately" is taken to mean±10%, ±5% or ±1% of a specified value. As used herein, the term "substantially" is taken to mean "to a large degree" or "at least a majority of" or "more than 50% of". Moreover, all ranges specified herein are inclusive of the range limits and all integer and fractional values therein especially as defined by the definition of the term "about".

As used herein, the term "prodrug" is taken to mean a compound that is administered in an inactive (or less than fully active) form, and is subsequently converted to an active pharmacological agent through normal metabolic processes. A prodrug serves as a type of 'precursor' to the intended drug, e.g. risperidone. Exemplary prodrugs include the fatty acid esters of paliperidone (9-hydroxyrisperidone) as disclosed in U.S. Pat. No. 6,555,544, the entire disclosure of which is hereby incorporated by reference. Preferred prodrugs and salts of paliperidone include those having a water solubility of less than or about 2 mg/ml.

As used herein, the term "derivative" is taken to mean a compound that is obtained by chemical modification of a parent compound such that the "derivative" includes within it almost all or all of the chemical structure of the parent (or base) compound. A derivative is a compound that is formed from a similar compound or a compound that can be imagined to arise from another compound, if one atom is replaced with another atom or group of atoms. A derivative is a compound derived or obtained from another and containing essential elements of the parent substance. A derivative is a chemical compound that may be produced from another compound of similar structure in one or more steps.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

The invention claimed is:

1. A gravimetric filling apparatus for use in gravimetric filling of one or more containers, said apparatus comprising:
   a) at least one receiver for said one or more containers, said at least one receiver comprising an upper receptacle adjoining a lower chamber for receiving said one or more containers, a first end, and a second end, wherein said receptacle has a larger diameter than said chamber;
   b) at least one lid for respective ones of said one or more receivers, said at least one lid comprising at least one charging port and said at least one lid being disposed at said first end; and
   c) at least one gravimetric system comprising a non-weighing surface and at least one abutment directed into said respective chamber and adapted to raise said one or more containers when said one or more containers are disposed within said chamber, and disposed at said second end, thereby forming contained space defined by said at least one receiver, said at least one lid, and said non-weighing surface, said contained space adapted for receiving said one or more containers, and said contained space being accessible through said at least one charging port for charging material therethrough into said one or more containers; and wherein said at least one abutment comprises at least one weighing element.

2. The apparatus of claim 1, wherein the gravimetric filling apparatus is further defined by at least one of the following: a) the length of said container combined with the height of said abutment is less than the length of said contained space; b) the apparatus is adapted for gravimetric filling of containers comprising one or more flanges or ridges, wherein the spatial volume of said receptacle is greater than the spatial volume of said one or more flanges or ridges; c) the spatial volume defined by the outer surfaces of said container is less than the spatial volume defined by the inner surfaces of said contained space; and/or d) the apparatus is adapted for gravimetric filling of containers comprising one or more flanges or ridges, wherein the height and inner diameter of said receptacle is greater than the height and outer diameter of said flange or ridge.

3. The apparatus of claim 1, wherein
said receiver has a height 4H and a first outer diameter 4OD, and said chamber has a first length 4L and a first inner diameter 4ID; and said receptacle is disposed at an upper end of said chamber, said receptacle has a first height 6H and a second inner diameter 6ID, and said receptacle is defined by a lower surface 6A and a circumferential surface 6B, wherein 4OD>6ID>4ID;
said at least one lid has an outer diameter 12OD, whereby the smallest outer diameter of said at least one lid is sufficient to cover the receptacle; and
said receiver is adapted to receive a container comprising:
   a) a body having a length 16H and an outer diameter 16OD and an inner cavity; and b) a flange, ring, or ridge disposed adjacent to or at an upper end of said body, said flange, ring, or ridge having a second height 3H and a second outer diameter 3OD, and said flange, ring, or ridge being defined by a lower surface and a circumferential surface, wherein 3OD>16OD and 16H>3H; and
wherein
6ID>3OD>4ID; and
4H>16H and 6H>3H.

4. The apparatus of claim 3, wherein said at least one abutment has a height 11H and an outer diameter 11OD, wherein: a) 4H>(16H+11H); and b) 4ID>11OD.

5. The apparatus of claim 3, wherein when said hollow receiver, said container, said lid, and said gravimetric weighing system are assembled, the lower surface of said flange, ring, or ridge is spaced away from said non-weighing surface, the upper surface of said flange, ring, or ridge is spaced away from the lower surface of said lid, and said circumferential surface of said flange, ring, or ridge is spaced away from said circumferential surface of said receptacle.

6. The apparatus of claim 3, wherein when said receiver, said container, said lid, and said gravimetric weighing system are assembled, the lower surface of said flange, ring, or ridge is spaced away from said non-weighing surface by the distance S1, the upper surface of said flange, ring, or ridge is space away from the lower surface of said lid by the distance S2, and said circumferential surface of said flange, ring, or ridge is spaced away from said circumferential surface of said receptacle by the distance S3.

7. The apparatus of claim 3, wherein 12OD>6ID or wherein 12OD>4OD>6ID.

8. The apparatus of claim 1 further comprising one or more sleeves disposed between the outer surface of the container and the inner surface of said chamber.

9. The apparatus of claim 1, wherein the receiver contacts or engages said non-weighing surface and the lower surface of said lid, thereby forming a contained space within the receiver.

10. The apparatus of claim 1 further comprising at least one of the following: a) control system that controls the amount of material charged into one or more containers; b) material charging system for charging material into one or more containers; c) laminar airflow system; d) deionizer; e) transfer system for transferring the material-containing container, with or without its respective receiver, to another operational area; or f) a combination of any two or more thereof.

11. The apparatus of claim 1, wherein said at least one abutment is selected from the group consisting of mount, projection, cup, stand, and platform.

* * * * *